United States Patent [19]

Baker et al.

[11] Patent Number: 5,166,215
[45] Date of Patent: * Nov. 24, 1992

[54] FUNGICIDAL PYRIDYL CYCLOPROPANE CARBOXAMIDINES

[75] Inventors: Don R. Baker, Orinda; Keith H. Brownell, San Jose, both of Calif.

[73] Assignee: Imperial Chemical Industries PLC, London, Great Britain

[ * ] Notice: The portion of the term of this patent subsequent to May 16, 2006 has been disclaimed.

[21] Appl. No.: 594,794

[22] Filed: Oct. 9, 1990

Related U.S. Application Data

[62] Division of Ser. No. 308,582, Feb. 10, 1989, Pat. No. 4,975,442, which is a division of Ser. No. 115,015, Oct. 29, 1987, Pat. No. 4,831,044.

[51] Int. Cl.$^5$ .................. A01N 43/40; C07D 213/74; C07D 213/75
[52] U.S. Cl. .................................... 514/345; 514/349; 514/352; 546/261; 546/264; 546/297; 546/306; 546/312
[58] Field of Search .............. 546/297, 291, 261, 264, 546/305, 306, 312; 514/345, 349, 332, 352

[56] References Cited

U.S. PATENT DOCUMENTS

4,831,044 5/1989 Baker et al. .................. 514/349
4,975,442 12/1990 Baker et al. .................. 514/332

*Primary Examiner*—Alan L. Rotman
*Attorney, Agent, or Firm*—William E. Dickheiser; Michael J. Bradley

[57] ABSTRACT

Novel fungicidal pyridyl cyclopropane carboxamidines having the general structural formula

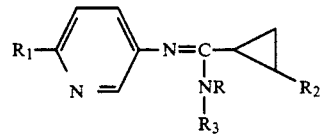

and tautomers thereof wherein
R is selected from the group consisting of hydrogen, pyridyl, substituted pyridyl, $C_1$-$C_3$ alkoxy, $C_1$-$C_6$ alkyl, acyl, carbamoyl, sulfonyl and cyano;
$R_1$ is selected from the group consisting of halogen, $C_1$-$C_3$ alkoxy and $C_1$-$C_3$ alkenyloxy;
$R_2$ is selected from the group consisting of hydrogen and $C_1$-$C_3$ alkyl;
$R_3$ is selected from the group consisting of hydrogen, alkyl, aryl or arylalkyl;
and fungicidally acceptable organic and inorganic salts thereof.

9 Claims, No Drawings

FUNGICIDAL PYRIDYL CYCLOPROPANE CARBOXAMIDINES

This is a divisional of application Ser. No. 07/308,582 filed Feb. 10, 1989, U.S. Pat. No. 4,975,442, which is a divisional of application Ser. No. 07/115,015, filed Oct. 29, 1987, U.S. Pat. No. 4,831,044.

BACKGROUND OF THE INVENTION

Fungal infection of crops such as barley, rice, tomatoes, wheat, beans, roses, grapes and other agriculturally important crops can cause heavy losses in both quantity and quality of agricultural products. It is therefore extremely desirable to have means of preventing, controlling or eliminating fungal growth. Much preventive spraying with commercial fungicides is conducted to attempt to prevent the establishment and growth of fungi on agriculturally important crops. It would also be desirable to have a curative fungicide which, on detection of fungal infection, could control the fungi and eliminate the deleterious effects by use of a postinfection curative spray.

SUMMARY OF THE INVENTION

Novel fungicidal pyridyl cyclopropane carboxamidines having the formula

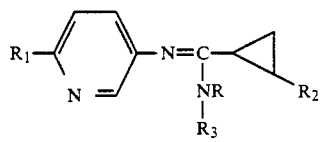

and tautomers thereof wherein
R is selected from the group consisting of hydrogen, pyridyl, substituted pyridyl, $C_1$-$C_3$ alkoxy, $C_1$-$C_6$ alkyl, acyl, carbamoyl, sulfonyl and cyano;
$R_1$ is selected from the group consisting of halogen such as chlorine, fluorine and bromine, $C_1$-$C_3$ alkoxy such as propoxy, ethoxy and methoxy, preferably methoxy and $C_1$-$C_3$ alkenyloxy;
$R_2$ is selected from the group consisting of hydrogen and $C_1$-$C_3$ alkyl, preferably methyl;
$R_3$ is hydrogen, alkyl, aryl or arylalkyl;
and fungicidally acceptable organic and inorganic salts thereof which are highly effective fungicides for use both as preventive and curative fungicides are disclosed herein.

When $R_3$ is hydrogen, the compounds of this invention can exist in the tautomeric form

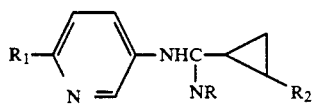

and the defined formula containing $R_3$ is to be considered as being inclusive of such tautomers.

The term "fungicide" is used to mean a compound which controls fungal growth. "Controls" includes prevention, destruction and inhibition of fungal growth. The term "curative" is meant to refer to a postinfection application of a fungicide which establishes control of fungal infection and prevents development of deleterious effects of the fungi on the host crop.

DETAILED DESCRIPTION

The novel fungicidal compounds of this invention are pyridyl cyclopropane carboxamidines having the general formula

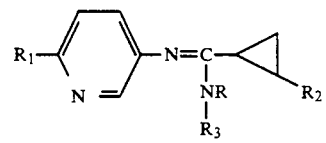

and tautomers thereof wherein
R is selected from the group consisting of hydrogen, pyridyl, substituted pyridyl, $C_1$-$C_3$ alkoxy, $C_1$-$C_6$ alkyl, acyl, carbamoyl, sulfonyl and cyano;
$R_1$ is selected from the group consisting of halogen such as chlorine, fluorine and bromine, $C_1$-$C_3$ alkoxy such as propoxy, ethoxy and methoxy, preferably methoxy and $C_1$-$C_3$ alkenyloxy;
$R_2$ is selected from the group consisting of hydrogen and $C_1$-$C_3$ alkyl, preferably methyl;
$R_3$ is hydrogen, alkyl, aryl or arylalkyl;
and fungicidally acceptable organic and inorganic salts thereof which are highly effective fungicides for use both as preventive and curative fungicides are disclosed herein.

When $R_3$ is hydrogen, the compounds of this invention can exist in the tautomeric form

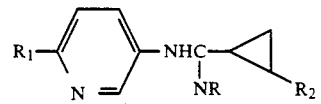

and the defined formula containing $R_3$ is to be considered as being inclusive of such tautomers.

The compounds of this invention can be generally prepared by a multi-step reaction process. The first step comprises reacting a properly substituted aminopyridine with the appropriately substituted cyclopropane carboxylic acid chloride in an inert solvent such as methylene chloride, chloroform hexane, or toluene in a suitable reaction vessel. It may be desirable to have an acid scavenger present during the reaction such as a pyridine, a trialkylamine, an alkaline carbonate or an alkaline hydroxide.

Depending upon the reaction conditions, the reaction will proceed at room temperature, but will operate at a temperature range from $-30°$ to $80°$ C. Depending upon the reaction temperature, the reaction will go to completion in up to about 3 hours. The resulting intermediate solid product can be isolated by conventional procedures such as washing with an alkaline solution, separation of the solid product by filtration if this intermediate product forms as a solid in the reaction, or by drying and evaporation of the reaction solution to give the desired first intermediate.

The second step comprises reaction of the dry product from the first reaction with an imidoylating reagent such as phosphorus pentachloride in an inert solvent such as methylene chloride or the like. The reaction can be run at room temperature or at the reflux tmperature of the methylene chloride. Evaporation of the solvent under vacuo gives the hydrochloride of the imidoyl chloride as the second intermediate.

This imidoyl chloride intermediate is reacted with excess ammonia, appropriately substituted amine or hydroxylamine in the cold at −30° to −80° C. in an inert solvent such as ether or methylene chloride. After the reaction is complete it is allowed to warm to room temperature and washed with water. Separation, drying and evaporation of the solvent gives the product, amidine.

This amidine-type product can also be further reacted in an inert solvent such as ether or methylene chloride with an appropriately substituted isocyanate. After completion of the reaction, the product can be isolated by evaporation of the solvent to give the desired carbamoyl amidine.

Also, the amidine-type product can be reacted further with the appropriate acid chlorides, sulfonyl chlorides, carbamoyl chlorides, or phosphoryl chlorides in an inert solvent such as methylene chloride, using an acid scavenger such as pyridine. After the appropriate water and/or bicarbonate wash, drying and stripping of the solvent yields the desired acyl, sulfonyl, carbamoyl, or phosphoryl amidine product.

EXAMPLE 1

Preparation of N-(2-Methoxy-5-pyridyl)-cyclopropane carboxamide

5-Amino-2-methoxy pyridine (12.4 g, 0.10 mol) and pyridine (10 ml) were mixed together in dichloromethane (200 ml) in a reaction flask. Cyclopropane carboxylic acid chloride (9.1 ml, 0.10 mol) was added to the reaction mixture over a period of 2 minutes. The reaction was exothermic and the temperature rose to 34° C. The reaction was allowed to stand for one hour at room temperature, after which the reaction mixture was wsahed with 5% sodium hydroxide (200 ml) and water (100 ml). The resulting organic phase was separated and dried over anhydrous magnesium sulfate. Crystals formed, so the mixture was filtered and washed with 300 ml of acetone and the filtrate evaporated in vacuo to give a solid that was triturated with hexane to yield 16.7 g, after drying. The product was identified by infrared (IR) and nuclear magnetic spectroscopy (NMR) analysis as the title compound, having a melting pont of 130°-131° C.

EXAMPLE 2

Preparation of 2-(Methoxy-5-pyridyl)-cyclopropane carboximidoyl chloride

Dichloromethane (50 ml) and phosphorus pentachloride (10.4 g, 0.05 mol) were mixed together in a reaction flask. N-(2-Methoxy-5-pyridyl)cyclopropane carboxamide (9.0 g, 0.05 mol) was added, under nitrogen, in portions to the reaction flask with stirring. The reaction was exothermic and was stirred at room temperature for one hour hour and then heated to reflux with stirring for an additional hour to dissolve and react the solids in the reaction vessel. The reaction mixture was then evaporated under vacuum to give a solid product that was washed twice using ether (50 ml portions) and dried under vacuum to yield 12.0 g of a solid, identified as the title compound by nuclear magnetic resonance spectra.

EXAMPLE 3

Preparation of N-(2-Methoxy-5-pyridyl)-cyclopropanecarboxamide

Excess ammonia gas was bubbled into a mixture of N-(2-methoxy-5-pyridyl)cyclopropanecarboximidoyl chloride (7.5 g) and methylene chloride (200 ml) at −40° C. over a period of 40 minutes. The reaction was allowed to warm to 10° C. and washed with water (50 ml), dried over anhydrous magnesium sulfate, filtered and evaporated in vacuo to give a solid that was washed with ether to give 2.5 g of the desired product m.p. 121°-124° C. The product was identified by IR, NMR and mass spectroscopy analysis.

Representative compounds of this invention and their properties are shown in Table I.

TABLE I

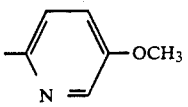

| Cmpd. No. | R | R₁ | R₂ | R₃ | $n_D^{30}$ or melting point °C. |
|---|---|---|---|---|---|
| 1 |  | —OCH₃ | —Cl | —H | 85.0° C. |
| | as the hydrochloride salt | | | | |
| 2 | —OCH₃ | —OCH₃ | —H | —H | oil |
| 3 | —CH₃ | —OCH₃ | —H | —OCH₃ | oil |
| 4 | —H | —OCH₃ | —H | —H | 121.0-124.0° C. |
| 5 | —C≡N | —OCH₃ | —H | —H | 144.0-146.0° C. |
| 6 | O<br>∥<br>—CNHCH₃ | —OCH₃ | —H | —H | 85.0-94.0° C. |
| 7 | 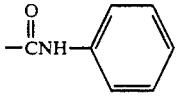 | —OCH₃ | —H | —H | 115.0-119.0° C. |

TABLE I-continued

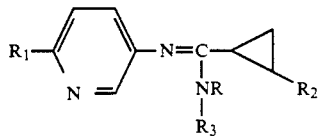

| Cmpd. No. | R | $R_1$ | $R_2$ | $R_3$ | $n_D^{30}$ or melting point °C. |
|---|---|---|---|---|---|
| 8 | —CNH—⟨⟩—Cl (O‖) | —OCH$_3$ | —H | —H | 81.0–88.0° C. |
| 9 | —CCF$_3$ (O‖) | —OCH$_3$ | —H | —H | 92.0–95.0° C. |

EXAMPLE 4

Preventative Spray Evaluation Procedures

Barley Powdery Mildew (BPM)

Northrup King Sunbar 401 barley seed is planted (12 seeds/2" pot) in a sandy-loam soil seven days prior to testing. The test compound is diluted in a 50/50 acetone/water solution to produce concentrations decreasing from 750 ug/ml. Twelve ml of test solution are sprayed onto the barley plants with atomizing sprayers.

Twenty-four hours later, test plants are placed in an inoculation box equipped with a circulating fan. Barley plants with heavily sporulating *Erysiphe graminis* lesions are placed in front of the fan to dislodge and distribute the spores. After two minutes the fan is shut off and the chamber is left closed five minutes for the spores to settle. Inoculated plants are then placed on an automatic sub-irrigation greenhouse bench.

Results are recorded seven days following inoculation as percent disease control based on the percent reduction in infected area as compared to the untreated control plants. Compound concentrations which provide 90% disease control (EC 90) are determined from dosage/dilution curves.

Rice Blast (RB)

Ten seeds of Calrose M-9 rice are planted in 2 inch pots in a sandy-loam soil 12 days prior to testing. The compound to be tested is diluted in a 50/50 acetone/water solution to produce concentrations decreasing from 750 ug/ml. Twelve ml of test solution are sprayed onto the rice plants with atomizing sprayers.

Inoculum is produced from 3 week old cultures of *Pyricularia oryzae*, grown on Rice Polish agar. The agar is first flooded with deionized water, the spores gently rubbed off the surface, and then diluted to $5 \times 10^5$ spore/ml in deionized water plux 0.05% Tween ®20. Twenty-four hours after compound application, plants are inoculated by spraying with the spore suspension to runoff, allowing it to dry on the leaves, respraying to run-off, and then placing the plants into a mist chamber. Following 48 hours of mist, the plants are moved to an automatic subirrigation greenhouse bench.

Results are recorded seven days following inoculation as percent disease control based on the percent reduction in lesion area as compared to the untreated control plants. Compound concentrations which provide 90% disease control (EC 90) are estimated from dosage/dilution curves.

Botrytis Bud Blight (BB)

Two white rose petals are placed in a petri dish lined with wet filter paper. The compound to be tested is diluted with a 50/50 acetone/water solution to produce concentrations decreasing from 750 ug/ml. One half ml of test solution is atomized onto the petals, and allowed to dry.

Inoculum is prepared by adding a 5 mm plug from a two-week old *Botrytis cinerea* culture grown on Elliot's V-8 agar, to 10 ml sterile distilled water plus 0.5 ml grape juice. A 20 µl drop of this inoculum suspension is placed on each petal. Petri dishes with inoculated petals are stored in sealed plastic boxes to maintain saturated humidity.

Results are read four days following inoculation as a percent reduction in necrotic area compared to the acetone/water controls. Compound concentrations which provide 90% disease control (EC 90) are determined from dosage/dilution curves.

The results are presented in Table II as an approximate EC 90 in parts per million (750 µg/ml equals 750 ppm). The entry (750) indicates partial control at 750 ppm. An asterisk (*) indicates no control at 750 ppm.

TABLE II

| Cmpd. No. | PM | RB | BB |
|---|---|---|---|
| 1 | (750) | * | 200 |
| 2 | * | * | 750 |
| 3 | 750 | * | 70 |
| 4 | * | * | 700 |
| 5 | * | * | 600 |
| 6 | 750 | (750) | 750 |
| 7 | (750) | * | * |
| 8 | * | * | (750) |
| 9 | * | * | 750 |

The compounds of this invention are particularly effective against Botrytis bud blight and are particularly effective as preventative foliar sprays and curative foliar sprays when compared to standard commercial compounds used as Botrytis preventative and curative sprays. Fungi on which the compounds of the present invention are particularly effective are *Erysiphe graminis* and *Pyricularia oryzae*.

The compounds of the present invention are useful as fungicides, especially as preventative or curative fungicides, and can be applied in a variety of ways at various concentrations. In general, these compounds and formulations of these compounds can be applied directly to the crop foliage, the soil in which the crop is growing or in the irrigation water for the crop or soil. In practice, the compounds herein defined are formulated into fungicidal compositions, by admixture, in fungicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active fungicidal compounds may be formulated as wettable powders, as emulsifiable concentrates, as powdery dusts, as solutions or as any of several other known types of formulations, depending upon the desired mode of application. Preferred formulations for preventative or curative fungicidal applications are wettable powders and emulsifiable concentrates. These formulations may contain as little as about 0.1% to as much as about 95% or more by weight of active ingredient. A fungicidally effective amount depends upon the nature of the seeds or plants to be treated and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the soil or plants either as a dry dust or as a dispersion in water or other liquid. Typical carriers for wettable powders include Fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent to facilitate wetting and dispersion.

Dry flowables or water dispersible granules are agglomerated wettable powders made by either pan granulation or by fluidized bed. The dry flowable is ultimately applied to the soil or plants as a dispersion in water or other liquid. These granules are dust-free and free flowing when dry and yet upon dilution in water, form homogeneous dispersions. Typical carriers for dry flowables include fuller's earth, kaolin clays, silicas and other readily wet organic or inorganic diluents. The dry flowables normally are prepared to contain from about 5% to about 95% of the active ingredient and usually contain a small amount of wetting, dispersing or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphtha, isophorone and other non-volatile organic solvents. For fungicidal application, these concentrates are dispersed in water or other liquid carrier and normally applied as a spray to the area to be treated. The percentage by weight of the essential active ingredient may vary according to the manner in which the composition is to be applied, but in general comprises about 0.1% to 95% of active ingredient by weight of the fungicidal composition.

Typical wetting, dispersing or emulsifying agents used in agricultural formulations include, for example, the alkyl and alkylaryl sulfonates and sulfates and their sodium salts; polyhydroxy alcohols; and other types of surface-active agents, many of which are available in commerce. The surface-active agent, when used, normally comprises from 0.1% to 15% by weight of the fungicidal composition.

Dusts, which are free-flowing admixtures of the active ingredient with finely divided solids such as talc, clays, flours and other organic and inorganic solids which act as dispersants and carriers for the toxicant, are useful formulations for many applications.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

| EXAMPLES OF TYPICAL FORMULATIONS | |
|---|---|
| Ingredient | Weight % |
| Oil | |
| Compound 1 | 1 |
| Oil solvent-heavy aromatic naphtha | 99 |
| Total | 100 |
| Emulsifiable Concentrate | |
| Compound 2 | 50 |
| Kerosene | 45 |
| Emulsifying agent (mixture of long chain ethoxylated polyethers with long chain sulfonate) | 5 |
| Total | 100 |
| Emulsifiable Concentrate | |
| Compound 3 | 90 |
| Kerosene | 5 |
| Emulsifying agent (mixture of long chain ethoxylated polyethers with long chain sulfonate) | 5 |
| Total | 100 |

| Dusts and/or Powders | | | |
|---|---|---|---|
| Ingredient | Wt. % | Wt. % | Wt. % |
| Compound 4 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

Other useful formulations for fungicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely divided form as a result of vaporization of a low boiling dispersant solvent carrier, such as the Freons, may also be used.

The fungicidal compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in low dosages.

We claim:

1. A compound having the structural formula

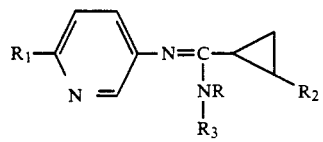

and tautomers thereof wherein

R is selected from the group consisting of hydrogen, $C_1-C_3$ alkoxy, $C_1-C_6$ alkyl and cyano $R_1$ is selected from the group consisting of halogen, $C_1-C_3$ alkoxy and $C_1-C_3$ alkenyloxy;

$R_2$ is selected from the group consisting of hydrogen and $C_1-C_3$ alkyl;

$R_3$ is selected from the group consisting of hydrogen or —$OCH_3$; or a fungicidally acceptable organic or inorganic salt thereof.

2. The compound of claim 1 wherein R is —C≡N, $R_1$ is —$OCH_3$, $R_2$ is —H and $R_3$ is —H.

3. The compound of claim 1 wherein R is —$CH_3$, $R_1$ is —$OCH_3$, $R_2$ is —H and $R_3$ is —$OCH_3$.

4. A fungicidal composition comprising a fungicidally effective amount of a compound having the structural formula

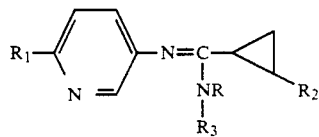

and tautomers thereof wherein

R is selected from the group consisting of hydrogen, $C_1-C_3$ alkoxy, $C_1-C_6$ alkyl and cyano $R_1$ is selected from the group consisting of halogen, $C_1-C_3$ alkoxy and $C_1-C_3$ alkenyloxy;

$R_2$ is selected from the group consisting of hydrogen and $C_1-C_3$ alkyl;

$R_3$ is selected from the group consisting of hydrogen or —$OCH_3$; or a fungicidally acceptable organic or inorganic salt thereof.

5. The method of controlling fungi comprising applying to the area where control is desired, a fungicidally effective amount of a compound having the formula

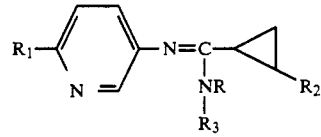

and tautomers thereof wherein

R is selected from the group consisting of hydrogen, $C_1-C_3$ alkoxy, $C_1-C_6$ alkyl and cyano $R_1$ is selected from the group consisting of halogen, $C_1-C_3$ alkoxy and $C_1-C_3$ alkenyloxy;

$R_2$ is selected from the group consisting of hydrogen and $C_1-C_3$ alkyl;

$R_3$ is selected from the group consisting of hydrogen or —$OCH_3$; or a fungicidally acceptable organic or inorganic salt thereof.

6. The fungicidal composition of claim 4 wherein R is —C≡N, $R_1$ is —$OCH_3$, $R_2$ is —H and $R_3$ is —H.

7. The method of claim 5 wherein R is —$CH_3$, $R_1$ is —$OCH_3$, $R_2$ is —H and $R_3$ is —$OCH_3$.

8. The method of claim 5 wherein R is —C≡N, $R_1$ is —$OCH_3$, $R_2$ is —H and $R_3$ is —H.

9. The fungicidal composition of claim 4 wherein R is —$CH_3$, $R_1$ is —$OCH_3$, $R_2$ is —H and $R_3$ is —$OCH_3$.

* * * * *